United States Patent

Müller et al.

[11] 4,315,672
[45] Feb. 16, 1982

[54] COMBINABLE APPARATUS FOR EXAMINATION OF THE EYE

[75] Inventors: Ortwin Müller, Königsbronn; Victor Stopar, Oberkochen, both of Fed. Rep. of Germany

[73] Assignee: Carl Zeiss-Stiftung, Oberkochen, Fed. Rep. of Germany

[21] Appl. No.: 55,511

[22] Filed: Jul. 9, 1979

Related U.S. Application Data

[63] Continuation of Ser. No. 777,514, Mar. 14, 1977, abandoned.

[30] Foreign Application Priority Data

Apr. 2, 1976 [DE] Fed. Rep. of Germany ....... 2614273

[51] Int. Cl.$^3$ .............................................. A61B 3/10
[52] U.S. Cl. ........................................ 351/13; 351/14; 351/6
[58] Field of Search ................................ 351/6, 13, 14

[56] References Cited

U.S. PATENT DOCUMENTS 3,290,927 12/1966 Gambs .................................. 351/13

Primary Examiner—John K. Corbin
Assistant Examiner—Rodney Bovernick
Attorney, Agent, or Firm—Hopgood, Calimafde, Kalil, Blaustein & Judlowe

[57] ABSTRACT

The invention contemplates eye-examination apparatus wherein modular-component construction enables a base with binocular-microscope viewing structure to selectively serve multiple-instrument functions, one of which is specifically an ophthalmometer. In the form described, the ophthalmometer component is a module which, when selected for use with the base module, provides a direct internally developed read-out of reflected-mire displacement in one of the two optical systems of binocular viewing and which provides via the other binocular optical system a concurrent display of the two reflected-mire images in the course of displacement adjustment; in the other selected employment of the base module, the instrument is a slit-lamp microscope. The ophthalmometer axis coincides with the central axis of symmetry of the slit-lamp microscope, so that no adjustment of the base module is needed in relation to a particular eye to make successive use of the same viewing structure in a slit-lamp mode and in an ophthalmometer mode.

4 Claims, 1 Drawing Figure

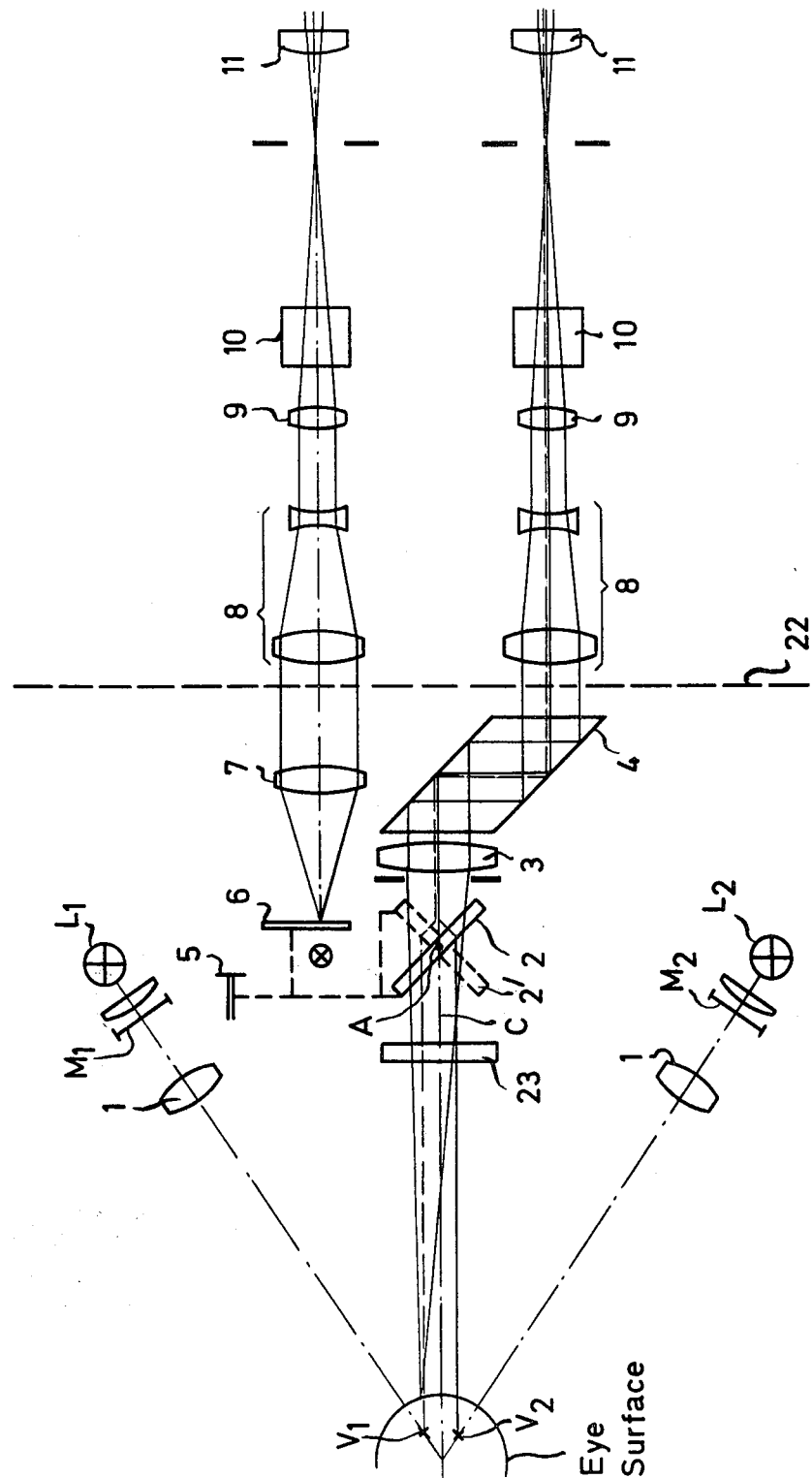

COMBINABLE APPARATUS FOR EXAMINATION OF THE EYE

This is a continuation of copending application Ser. No. 777,514, filed Mar. 14, 1977 now abandoned.

The present invention relates to a combinable apparatus for the examination of the eye.

Standard instruments of the ophthalmologist include the ophthalmometer, the slit lamp and the operating microscope. Curvatures of the cornea and lens are measured with the ophthalmometer, and very fine details of the front section of the eye are made visible by the slit lamp. The slip lamp and the operating microscope have been developed as a stereo microscope and operate in accordance with the principle of a telescopic magnifier.

To date, the ophthalmometer and the slit lamp have been considered and produced as completely different and separate instruments, owing to their essential differences. Thus, for the diagnosis of one and the same patient, the ophthalmologist uses two entirely separate instruments, which are arranged either on separate instrument supports or on a so-called double base. The disadvantages of these separate instruments consist of a high purchase price and the taking up of a large amount of space.

The object of the present invention is to provide a combination or combinable instrument, involving modular subassemblies, whereby the cost of the apparatus is reduced by saving all construction parts which would otherwise be functionally present in duplicate.

This object is achieved in accordance with the invention by so combining an ophthalmometer subassembly (or module) with a binocular viewing microscope subassembly (or module) that the optical system of the ophthalmometer can be substituted for the main objective of a slit-lamp system which can otherwise use the same binocular viewing microscope subassembly (or module). This substitution of an ophthalmometer module for a slit lamp objective module enables the same eye of the same patient to be selectively viewed through the same binocular microscope, for the purposes served by the respective instruments but without any set-up change for the microscope or the patient.

In one suitable embodiment of the invention, the respective reflected-mire beam paths of the ophthalmometer are associated with one of the telescopes of the binocular viewing microscope module, and the beam path of the reading-lens system for the reflected-mire adjustment scale of the ophthalmometer is associated with the other telescope of the binocular viewing microscope module.

The advantages obtained with the invention consist, in particular, in the saving of structural parts for known methods of examination and, together therewith, the taking up of less space. Furthermore, by the combination, in accordance with the invention, of an ophthalmometer with a binocular viewing instrument, new fields of use are opened up for the ophthalmometer. Thus, for instance, the combination of ophthalmometer and operating microscope results in an operating ophthalmometer which was previously not available.

DETAILED DESCRIPTION

The accompanying drawing is a diagram schematically indicating optical components of an ophthalmometer incorporating an illustrative example of the invention.

In the form shown in the drawing, an ophthalmometer lens-system module of the combination instrument of the invention consists essentially of collimators 1, a doubling device 2-2', an objective 3, a prism 4, the measurement drive wheel 5, an inner dial or scale 6, and a magnifier objective 7. A first mire $M_1$ is projected by lamp $L_1$ (and its associated lens 1) for eye-surface reflection to the doubling device 2-2', and a second mire $M_2$ is projected by lamp $L_2$ (and its associated lens 1) for similar eye-surface reflection to device 2-2'; and device 2-2' comprises like plane-parallel glass plates mounted for ganged counter-rotational adjustment by the means 5, about an adjustment axis A, it being understood that the conventional ophthalmometer hardware (not shown) for mounting the two mire-projection systems for rotation about the central ophthalmometer axis C also mounts the doubling device 2-2' as to maintain the adjustment axis A perpendicular to the plane of the mire-projection axes. The separation line 22 symbolizes mechanical separating or connecting means between two modules, enabling the described ophthalmometer subassembly to be selectively connected (as a module) to a stereo microscope module, namely the telescopic magnifier which otherwise serves the main objective of a slit-lamp system. For slit-lamp purposes, the main objective is located to the left of the dividing line 22 in the drawing, but it is removed for the presently described combination of instrument subassemblies or modules. The microscope module or base instrument, selectively combinable with the ophthalmometer module, thus comprises magnification changers 8, tube objectives 9, prism inversion systems 10, and oculars 11.

It can be noted from the drawing that functionally one microscope telescope is used for the reflected-mire measurement beams and the other microscope telescope serves the reading-lens system for the adjustment scale, thus producing an ophthalmometer with so-called internal reading. The purpose of the prism 4 is to make possible an arrangement with rotational symmetry which, as noted above, is a characteristic ophthalmometer feature; in other words, the axial offset achieved by prism 4 is such as to locate the ophthalmometer module axis C midway between the respective telescope axes. The magnification changers 8 are also advantageously used in making measurements with the described ophthalmometer, to suit the examination of smaller or larger radii of eye-surface curvature; in prior-art devices, it had been necessary to change the ocular of the ophthalmometer for best examination of different radii of curvature.

It will be appreciated that although the described apparatus provides a Helmholz ophthalmometer which measures eye-surface radius upon adjusted registration of reflected-mire images and in a manner independently of distance, the invention is not limited to this specific example. A combination instrument in accordance with the invention can also be constructed from ophthalmometers of different types, and using other binocular-telescope systems as the microscope base instrument or module. The module-separating and connecting means indicated schematically at 22 is seen from the drawing to cut both the collimated-light region (1) between objective 3 (as offset by prism 4) and its associated half of the microscope module or base instrument and (2) the collimated-light region between objective 7 and its associated other half of the microscope module. The separable means suggested at 22 thus makes it possible readily to restore the function of the original ophthalmological instrument, for example the indicated original slit-lamp system, by disconnection and insertion of instrument parts or modules.

What is claimed is:

1. An ophthalmometer module as an article of manufacture for use with a binocular-microscope module having two telescope systems with a predetermined spacing between the axes of said systems; said ophthalmometer module comprising ophthalmometer components, including an objective and an adjustable doubling device on an optical axis adapted for alignment with an eye to be examined, two mire-projecting systems symmetrically positioned and diametrically opposed with respect to said axis for concurrent direction at the eye to be examined, said ophthalmometer module including an axis-offsetting prism between its objective and the telescope systems, the axis-offsetting extent of said prism being half the spacing between axes of the telescope systems, and the orientation being such as to align the offset axis of said prism with one of the telescope axes when the said optical axis is aligned midway between the telescope axes.

2. The instrumentation of claim 1, in which said mire-projecting systems and said doubling device are rotatable about said optical axis.

3. The ophthalmometer module of claim 1, further including selectively operable means for adjusting said doubling device, and adjustment-indicating means including a scale and an objective lens on a scale-reading axis which is parallel to the offset axis of said prism and which is offset from said optical axis to the equal but opposite extend of the prism offset, whereby said scale-reading axis is aligned with the other telescope axis when said optical axis is aligned as aforesaid.

4. In combination, an ophthalmometer module as an article of manufacture and a binocular-microscope module as an article of manufacture for use with said ophthalmometer module, said binocular-microscope having two telescope systems with a predetermined spacing between the axes of said systems; said ophthalmometer module comprising ophthalmometer components, including an objective and an adjustable doubling device on an optical axis adapted for alignment with an eye to be examined, two mire-projecting systems symmetrically positioned and diametrically opposed with respect to said axis for concurrent direction at the eye to be examined, said ophthalmometer module including an axis-offsetting prism between its objective and the telescope systems, the axis-offsetting extent of said prism being half the spacing between axes of the telescope systems, and the orientation being such as to align the offset axis of said prism with one of the telescope axes when the said optical axis is aligned midway between the telescope axes; selectively operable means for adjusting said doubling device, and adjustment-indicating means including a scale and an objective lens on a scale-reading axis which is parallel to the offset axis of said prism and which is offset from said optical axis to the equal but opposite extent of the prism offset, whereby said scale-reading axis is aligned with the other telescope axis when said optical axis and prism offset are aligned as aforesaid, and whereby collimated light characterizes each module-to-module axis alignment between the spaced objectives thereof.

* * * * *